May 4, 1926. Re. 16,345
C. SHEARD
TRIAL FRAME
Original Filed July 3, 1922 2 Sheets-Sheet 1
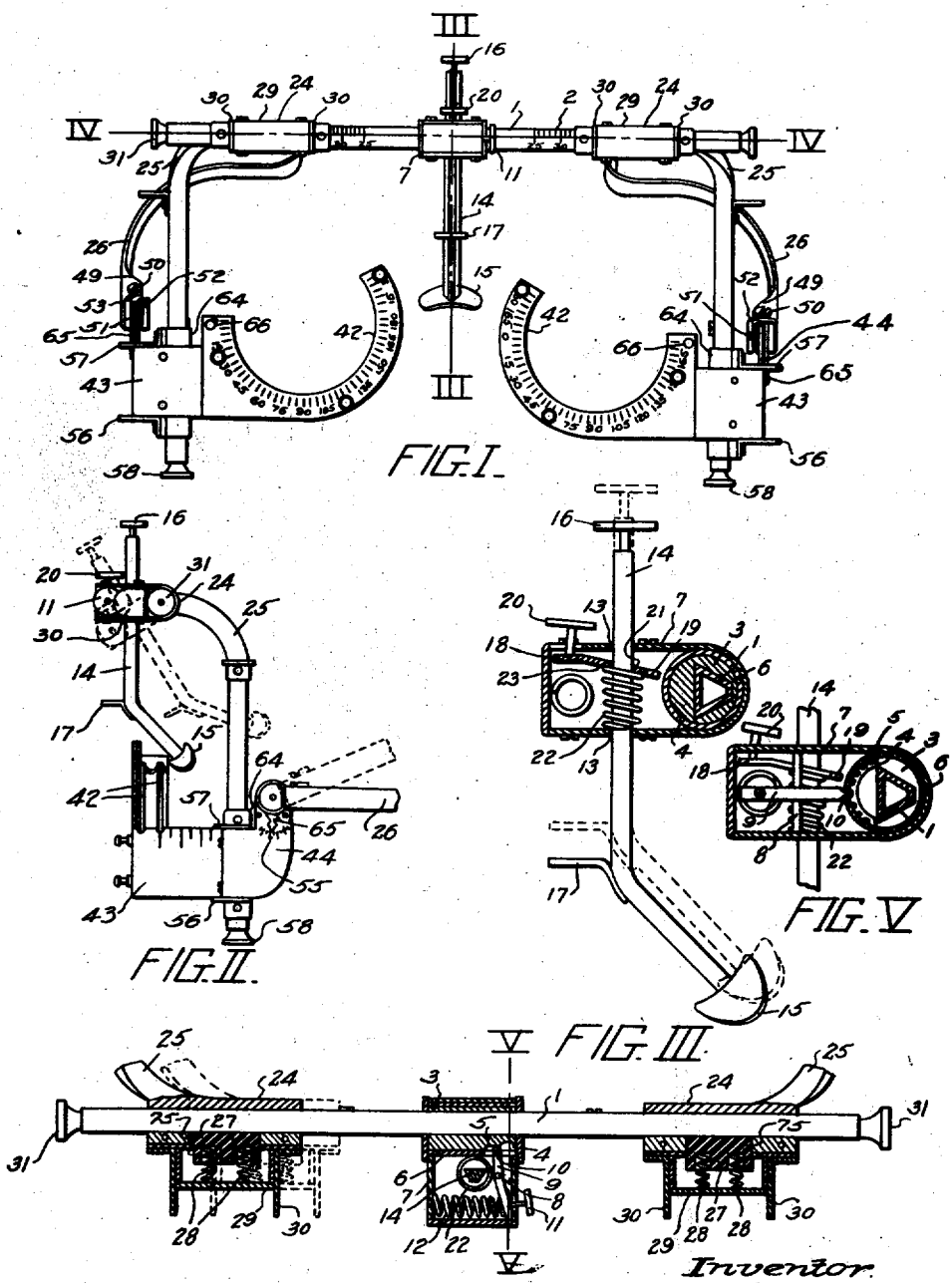
FIG. I.
FIG. II.
FIG. III.
FIG. V.
FIG. IV.
Inventor
Charles Sheard.
BY Harry H. Styll
ATTORNEY May 4, 1926. Re. 16,345
C. SHEARD
TRIAL FRAME
Original Filed July 3, 1922 2 Sheets-Sheet 2
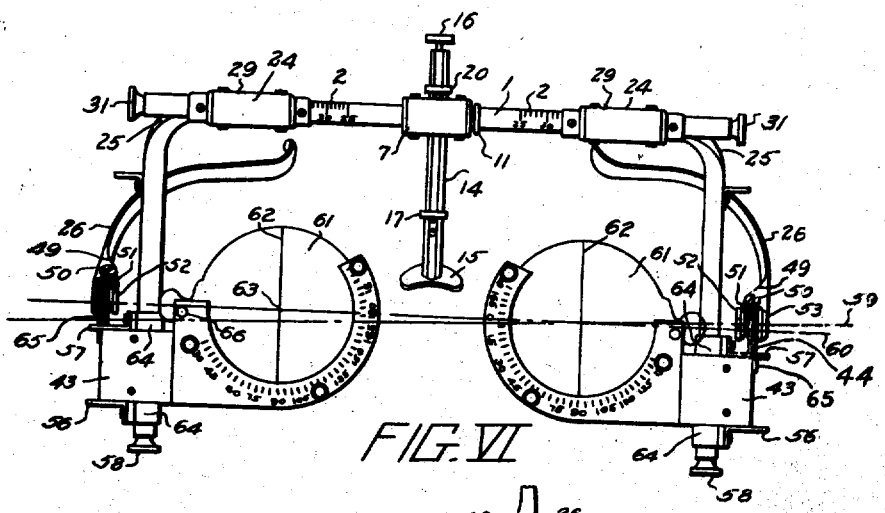
FIG. VI
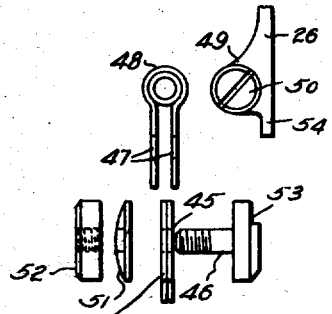
FIG. VII
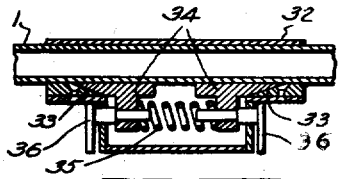
FIG. VIII
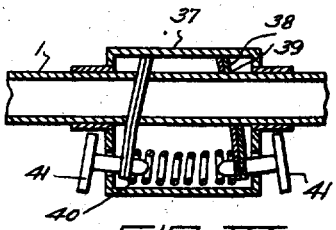
FIG. IX
Inventor.
Charles Sheard.
By Harry H. Styll
ATTORNEY.

Reissued May 4, 1926.

Re. 16,345

UNITED STATES PATENT OFFICE.

CHARLES SHEARD, OF ROCHESTER, MINNESOTA, ASSIGNOR TO AMERICAN OPTICAL COMPANY, OF SOUTHBRIDGE, MASSACHUSETTS, A VOLUNTARY ASSOCIATION OF MASSACHUSETTS.

TRIAL FRAME.

Original No. 1,557,347, dated October 13, 1925, Serial No. 572,632, filed July 3, 1922. Application for reissue filed March 23, 1926. Serial No. 96,892.

*To all whom it may concern:*

Be it known that I, CHARLES SHEARD, a citizen of the United States, residing at Rochester, in the county of Olmsted and State of Minnesota, have invented new and useful Improvements in Trial Frames, of which the following is a specification.

This invention relates to improvements in trial frames, which is to say, adjustable lens holding frames or members for use in supporting lenses to test the vision of a patient.

One of the principal objects of the present invention is the provision of a new or novel construction of trial frame which shall eliminate the use of gears, screws, and other adjusting devices as ordinarily employed in shifting the several parts of the frame to fit them to the face of a patient.

A further object of the invention is the provision of an improved simplified frame capable of universal adjustment in an extremely simple manner, facilitating the speed of conducting the examination and increasing the comfort of the patient, both on account of the lightness of frame made possible by the present improvements, and also the speed and ease with which the adjustments may be made without undue pulling or twisting of the frame on the face.

A further object of the invention is the provision of new and novel means for securing the parts in desired adjusted relation.

Other objects and advantages of the present invention should be readily apparent by reference to the following specification taken in connection with the accompanying drawings, and it will be understood that I may make any modifications in the specific details of construction shown and described within the scope of the appended claims without departing from or exceeding the spirit of the invention.

Figure I represents a front view of a frame embodying my improvements.

Figure II represents a side elevation thereof.

Figure III represents a sectional view as on the line III—III of Figure I, the bridge bar proper being shown in elevation.

Figure IV represents a horizontal sectional view as on line IV—IV of Figure I.

Figure V represents a detailed section taken on the line V—V of Figure IV.

Figure VI represents a front view showing a different use of my improved frame.

Figure VII represents a view of the several parts forming the end piece construction in position for assembly.

Figure VIII represents a sectional view of a modified form of locking device.

Figure IX represents a similar view illustrating another form thereof.

In the drawings, in which similar characters of reference are employed to denote corresponding parts throughout the several views, the numeral 1 designates the main or central bar member, preferably substantially triangular in cross section, as is indicated in Figures III and V, and being provided with the graduations 2 forming scales for determination of relative adjustment of certain of the remaining parts. This bar 1 has centrally secured thereon the block 3 substantially cylindrical in form, and having at one side a cut away portion or recess 4 and adjacent thereto the toothed or rack portion 5. Rotatably mounted upon the block 3 is the sleeve 6 to which is secured the nose rest guide 7. The member 7 has pivotally mounted therewithin, as at 8, the lever 9 formed at one end with the pawl portion 10 for interlocking engagement with the teeth 5 forming the rack and having at the opposite end the operating button 11. In operation the button 11 is pressed to rock the lever 9 against the pressure of the spring 12 and bring the end of the pawl into the end of the recess 4. When in this position the nose rest guide or carrier 7 and sleeve 6 may be easily and freely rotated upon the block 3, while upon release of the button 11 the spring 12 will reversely rock the lever causing the pawl 10 to interlock between certain of the teeth 5 as is indicated in Figure V, securely locking the device against any accidental rotative movement as respects the bar 1.

The member 7, it will be noted, is formed with the guide apertures 13 through which slide the nose rest bar 14 provided with the crest engaging portion 15 at the lower end and with the handle or actuating portions 16 and 17, respectively. To lock the member 14 against accidental sliding position and hold it in desired adjustment, I preferably make use of the locking plate 18 pivoted to the member 7, as at 19, and having on one end the actuating piece or button 20, and formed near the other end with the aperture 21 through which the member 14 slides. The member 19 is so disposed that when the aperture 21 which is somewhat larger than the apertures 13, is in alinement with said apertures the plate 18 is swung at a downward angle and against the pressure of the spring 22 which tends to swing the plate upward; this upward movement on account of the position of the point of pivotance causes the inner edge of the plate, as at 23, to bind against the member 14, any upward movement tending to increase this binding action so that the member 14 is securely locked in depressed position. To lower the member it is merely necessary to make use, for example, of the bottom of the casing 7 as a rest for the thumb, and press with the forefinger on the button 16, when the member 14 will readily slip downward. To move the parts into reverse position it is merely necessary to grasp the button 20 and handle or projection 17 between the thumb and forefinger and slide the bar 14 upward the desired amount, this pressure releasing the lock so that the bar will slide freely, while being automatically secured at the desired adjustment when the grip or pressure on the button 20 is released.

It will thus be seen that the exact position of the crest rest 15 as respects the bar 1 may be readily adjusted as desired in an extremely simple and efficient manner, the positioning of the bar 1 as respects the face, therefore, being dependent on the engagement between the crest member 15 and the nose of the patient.

Slidably mounted upon the bar 1 are the sleeves 24 having secured thereto the rearwardly and downwardly extending arms 25 adapted to support the lens cells and the temples 26 which serve to retain the frame in position on the face. The sleeves are each provided with a suitable friction device for holding them in desired adjusted position along the bar 1, while similar sleeve members 64 are slidably engaged on the arms 25 and provided with like friction devices for holding the individual cells in adjusted position along the arms. As these structures may be identical in form it is thought a description of the friction device in connection with the member 24 will be sufficient, it being understood that a similar friction device of any desired type is employed in connection with each of the sleeve or guide members 64.

In Figure IV, I have illustrated the sleeve as provided with a cut away or recessed portion, as at 75, in which is fitted the friction break block 27 actuated as by the pair of springs 28 contained within the small ornamental casing 29, having extending upwardly therefrom the ears or actuating handle portions 30. In operation the springs 28 bear against the friction block 27 which may be of fiber or other material sliding it inward in the notch or socket 75 and causing it to bind the sleeve 24 against the member 1. To move the device outward, however, it is merely necessary to grasp one of the members 30 with the thumb or forefinger and with the other of said members press against the rest 31 on the end of the bar 1, to slide the sleeve 24 and associated parts outwardly, while similar inward movement can be imparted by similar grasping with the hand of the member 7 and the opposite ear, this serving to press or slide the parts inward without twisting or pulling the frame appreciably on the face of the patient.

An alternative form of friction device is illustrated in connection with Figure VIII, in which the sleeve 32 corresponding to the sleeve 24 is made use of, but is provided with the bevel or undercut surfaces 33 against which ride the corresponding surfaces of the cam blocks 34 which are actuated by the intermediately disposed spring 35, and adapted to be pressed inwardly against the pressure of the spring and out of engagement with the inclined surfaces 33 of the member 32 as by the projecting handle portions 36, so that pressure against the two handle portions 36 will release the friction and allow the slide to be adjusted as desired.

A further modification is illustrated in connection with Figure IX, in which a corresponding sleeve member 37 is made use of sliding on the bar 1 and containing therewithin the tilting lock members 38 apertured as at 39 to receive the bar 1 and preferably secured to the casing for pivotal or rocking movement therewithin. In this case also an interposed spring 40 is employed which throws the plates apart as respects their lower or handle bearing portion so that as the two actuating handles or buttons 41 are pressed together they will swing the plates against the action of the spring 40 to release the member 1 so that the sleeve 37 may be readily slipped therealong, being automaticaly locked in place as the members 41 are released.

I would call particular attention to the fact that in connection with the present improved frame in place of the lens cell arms depending from the cross bar 1, as has hitherto been the custom, these arms are rearwardly and laterally curved and are primarily designed to be disposed at the sides of the face rather than entirely in front of the face, as has been the case with prior art constructions and to cause the lens holding pin or groove portions, as indicated at 42, to lie much closer to the face and in a position tending to best balance the frame on the face with a slight tendency to swing inward at the bar rather than outward, thus causing the same to cling and fit better to the face, as well as to allow better accurate positioning of the lenses before the eye at predetermined distances irrespective of the shape of the face or features of the patient. The lens cells are carried by arms or blocks 43 which are in turn secured to the guide sleeve members 42 and are provided with the rearward extensions 44 perforated as at 45 to receive the pivot screw or bolt 46 which also passes through the pivot apertures in the ears 47 of the temple attachment 48 which thus forms a hinge eye to interlock with the hinge ears 49 of the retaining temple 26 pivotally secured to the portion 48 as by the screw 50. A spring washer 51 and nut 52 serve to engage and secure the bolt in place, the bolt having the head portion somewhat flattened off, as is indicated at 53, so that the projecting terminus 54 of the temple may interlock therewith. The bolt head is further provided with the depending pointer portion 65 adapted to cooperate with the protractor scale 55 on the ear or plate portion 44 to indicate the angle to which the temple has been adjusted, as is most clearly shown in connection with Figure II of the drawings.

The present frame is designed for two types of testing, this being one of the particular reasons for having the angular adjustment of the temple just referred to. That is to say, the structure may be either employed as is indicated in Figure I of the drawings with the bar 1 substantially horizontal on the face and the difference if any in height of the two eyes compensated for by vertical sliding of the respective sleeves 64 on their supporting arms 25, which is accomplished by grasping of the projecting ears 56 or ear 57 and button or head 58, respectively, or the temples may be differently tilted so as to throw the frame itself in angular relation to the face but center each cell before the eye of the patient. This is indicated in Figure VI, in which the line 59 shows the normal horizontal axis and the line 60 the axis to which the frame is tilted. The amount of tilt necessary is determined in this instance through the use of the transparent discs 61 which are mounted in the proper lens cells or grooves 42 and are provided with the intersecting lines 62 determining the center point 63 which is supposed to be in line with the pupil of the eye at each side, this indicating that the frame is then in proper relation to the face for the testing purpose.

It will thus be seen that the present frame properly lends itself to either form of testing and that the action of the friction washer in connection with the bolt 46 and nut 52 and the interlocking of the temple with the bolt serves to frictionally hold the temple in desired position and thus regulate or control the tilt of the frame itself.

From the foregoing specification taken in connection with the accompanying drawings, the construction and purpose of my improved trial frame should be readily apparent, and it will be seen that I have provided an extremely satisfactory and desirable construction in which all adjustments may be accomplished by the use only of the thumb and forefinger and with a direct sliding action as opposed to a screw feed action, and in which means are provided in every instance so that this sliding action in either direction may be accomplished without necessity of steadying or pushing the frame with more than one hand of the examiner, and may be accomplished without necessity of removing the frame from the face or disturbing the frame to an amount appreciable or objectionable to the patient.

I would further call attention in connection with Figure I to the fact that the arcuate members 42 at each side are provided with upstanding lug portions 66 for the supporting pin 67 which lugs extend respectively to the zero point of the degree scale at the eye on the left, and the 180 degree point on the eye at the right. The purpose of this is so that the frame may be used in accordance with the system of testing particularly exemplified in Figure VI but in place of the employment of the transparent discs 61, a ruler or like gauge or wire may be placed to rest on the pins 66 when the same will extend along the zero-180 degree line of each eye or lens cell of the frame. This line or gauging member may be exactly lined up with the center of the pupils of each of the eyes, the frame being angled and adjusted to accomplish these results as with the discs of Figure VI.

I claim:

1. In a device of the character described, the combination with a central bar and a vertically and angularly adjustable nose rest support associated therewith comprising a block, a sleeve rotatably arranged around the block, means carried by the sleeve to prevent rotation thereof upon the block, and friction means for securing the nose rest support in desired vertically adjusted position and a positive release for the friction lock to disengage the same when it is desired to raise the nose rest support.

2. A trial frame including a supporting bar, a sleeve adjustable along the bar, a friction device for securing the sleeve in desired adjusted position, and handle projections on the sleeve and bar for cooperative employment in relative shifting of the parts against the action of the friction.

3. In a device of the character described, the combination with a central bar, of a vertically and angularly adjustable nose rest support associated therewith, friction means for securing the nose rest support in desired vertically adjusted position, the friction device and nose rest support having projecting portions adapted to be cooperatively engaged to facilitate imparting relative sliding movement to the parts.

4. In a device of the character described, the combination with a support, of a casing rotatable thereon, a nose rest bar carried by the casing, a laterally releasable rack mechanism for locking the casing against angular adjustment relative to the support, and a vertical releasable friction mechanism for locking the nose rest support against upward movement.

5. In a device of the character described, the combination with a support and a bar slidable relative to the support, of a movable friction device automatically disengaging on the movement of the bar in one direction and automatically locking to prevent movement of the bar in the opposite direction.

6. In a device of the character described, the combination with a supporting bar, of rearwardly and downwardly curving carrier arms associated therewith, forwardly extending lens cell portions on the supporting arms, rearwardly extending brackets on the arms, and angularly adjustable temple members carried by the brackets.

7. A device of the character described, comprising a central bar, a pair of slides on the bar, arms depending from the slides, lens holder members having portions slidably engaged on the arms and independent friction devices carried by each of the slides for locking its respective member in desired adjusted position.

8. In a device of the character described, the combination with a support and a bar slidable relative to the support, of a movable friction device automatically disengaging the movement of the bar in one direction and automatically locking to prevent movement of the bar in the opposite direction, and means to tilt the bar and to lock the same in the desired adjustment.

9. In a device of the character described, comprising the combination of a central bar, of a block rigidly mounted thereon, a sleeve arranged around the block, a nose rest guide carried by the sleeve, a nose engaging member slidable through the guide, means to prevent movement thereof through the guide in one direction, and means to lock the sleeve against rotation.

10. A device of the character described, comprising a central bar, a pair of slides on the bar, friction means carried by the slides to engage the bar to prevent accidental displacement, arms depending from the slides, lens holder means having members slidably engaged on the arms and independent friction devices carried by the lens holder means to prevent accidental displacement thereof on the depending arms.

11. A device of the character described, comprising a central bar, an adjustable nose engaging member carried thereby, friction members arranged on both sides of the nose engaging member, ears carried by the friction members to facilitate movement thereof along the bar, depending arms carried by the friction members, lens cells carried by the depending arms and friction means associated with the lens cells to maintain the lens cells in desired adjustment on the depending arms.

12. A device of the character described, comprising a central bar, a nose engaging member adjustably mounted thereon, friction means slidable on the bar, ears carried thereby to facilitate operation of the friction devices along the bar, rearwardly curved depending arms carried by the friction devices, lens cells associated with the depending arms, friction devices carried by the lens cells to prevent accidental displacement, ears carried by the said friction devices to facilitate movement of the friction devices along the depending arms, and stationary members carried by the depending arms for engagement when moving the lens cells.

13. In a device of the character described, the combination with a central bar, of a sleeve adjustable along the bar, frictional means carried by the sleeve adapted to contact with the bar to prevent displacement thereof, and ears carried by the said sleeve to facilitate the movement thereof along the bar when desired.

14. In a device of the character described, the combination with a central bar, of a block arranged on the bar, a sleeve rotatably mounted on the block, a nose engaging guide member formed integral with the sleeve, a nose engaging member in the guide member, a plate pivotally mounted within the guide member and having an opening adapted to receive the nose engaging member, an operating button having contact with one end of the plate adapted to force the said plate into an inoperative position and spring means contacting with the plate for normally urging the same into an operative position whereby to prevent movement of the nose engaging member in one direction.

15. In a device of the character described, the combination with a central bar of a block having gear teeth formed thereon, arranged on said central bar, of a housing around said block, a nose engaging member in the housing, a pivoted lever adapted for engagement with said gear teeth normally preventing displacement of the housing and the nose engaging member.

16. In a device of the character described, the combination with a central bar, of a block having gear teeth formed thereon, a sleeve rotatably arranged around the block, a nose engaging guide member formed integrally with the sleeve, a nose engaging member slidable through the guide member, a pivoted pawl adapted for engagement with the gear teeth to prevent rotation of the sleeve around the block and a pivoted plate adapted for engagement with the nose engaging member to normally hold the same against movement in one direction and means to move the said plate into an inoperative position.

17. In a device of the character described, the combination with a central bar, of a vertically and angularly adjustable nose rest support associated therewith, friction means for securing the nose rest support in desired vertical adjusted position, a positive release for the friction lock to disengage the same when it is desired to raise the nose rest support, a pair of slides on the bar, friction means associated therewith to prevent accidental displacement, rearwardly curved depending arms carried by the slides, lens holder members having portions slidably engaged on the arms, independent friction devices carried by each of the slides for locking its respective member in desired adjusted position, and adjustable temples carried by the said slides.

18. In a device of the character described, a cross bar, a slide thereon having an arm secured thereto extending rearwardly and downwardly from the cross bar, a slide on the downwardly projecting portion, an arm on the second slide, and a lens cell carried by the arm.

19. In a device of the character described, a cross bar having a finger rest thereon, a friction slide on the cross bar having a finger rest at each end, a support attached to the friction slide and extending to the rear and downwardly therefrom, a finger stop on the lower end of the depending arm, a second finger stop on the depending arm intermediate of its ends, a friction slide on the depending arm between the finger stops, finger stops on either end of the said second slide, an arm attached to the said second slide and a lens cell carried by the arm.

20. In a device of the character described, a cross bar, a block rotatably mounted on the cross bar, a stop to lock the block in any desired position on the cross bar, a post slidable through the block and a lock stop adapted to lock the slidable post against upward movement through the block and a nose rest on the lower end of the post.

21. In a device of the character described, a cross bar, a slide on the cross bar, a bar secured on the slide extending rearwardly and downwardly therefrom, a slide on the downwardly extending portion of the support having arms secured thereto, lens cells carried by the arms, means for moving the slide along the cross bar, and means for moving the slide along the depending support.

22. In a device of the character described, a side bar having a fixed finger rest thereon, a slide on the slide bar and a finger rest on the slide whereby the slide may be moved along the slide bar by placing one finger on the slide rest on the bar and another finger on the slide rest on the slide.

CHARLES SHEARD.